United States Patent [19]

Gealow

[11] Patent Number: 5,222,980
[45] Date of Patent: Jun. 29, 1993

[54] IMPLANTABLE HEART-ASSIST DEVICE

[75] Inventor: Kendra K. Gealow, Minnetonka, Minn.

[73] Assignee: Medtronic, Inc., Fridley, Minn.

[21] Appl. No.: 766,942

[22] Filed: Sep. 27, 1991

[51] Int. Cl.$^5$ .............................................. A61M 1/12
[52] U.S. Cl. ......................................... 623/3; 623/26; 600/18; 417/474
[58] Field of Search ................... 417/474, 475; 600/18, 600/16, 17; 623/3, 26, 37

[56] References Cited

U.S. PATENT DOCUMENTS

| | | | |
|---|---|---|---|
| 2,606,500 | 8/1952 | Schmidt | 417/474 X |
| 3,429,266 | 2/1969 | Jones | 600/16 X |
| 3,692,018 | 9/1972 | Goetz et al. | 417/475 X |
| 3,720,485 | 3/1973 | Holman | 417/475 X |
| 3,885,251 | 5/1975 | Pedroso | 623/3 |
| 3,955,557 | 5/1976 | Takagi | 600/16 |
| 4,014,318 | 3/1977 | Dockum et al. | 623/3 X |
| 4,453,537 | 6/1984 | Spitzer | 623/3 |
| 4,809,676 | 3/1989 | Freeman | 623/3 X |
| 4,938,766 | 7/1990 | Jarvik | 623/3 |
| 4,968,293 | 11/1990 | Nelson | 600/16 |
| 4,979,936 | 12/1990 | Stephenson et al. | 600/16 |

FOREIGN PATENT DOCUMENTS

| | | | |
|---|---|---|---|
| 1175431 | 3/1959 | France | 417/474 |
| 2527435 | 12/1983 | France | 600/16 |
| 2640698 | 6/1990 | France | 417/474 |

Primary Examiner—Randall L. Green
Assistant Examiner—D. Willse

Attorney, Agent, or Firm—Harold R. Patton; John A. Rissman; Gregory P. Gadson

[57] ABSTRACT

An implantable heart-assist device including extra-aortic balloon pump (EAB pump) for use in cooperation with a fluid pump is disclosed. The extra-aortic balloon pump includes a rigid, generally cylindrical housing and a flexible, generally cylindrical diaphragm residing generally within a longitudinal passageway in the rigid housing and secured to the rigid housing so as to create a plurality of separate expansion chambers. A plurality of fluid communication ports are provided for passing fluid into and out of the respective expansion chambers. The rigid housing includes interior and exterior surfaces, proximal and distal ends, and a longitudinal passageway. The diaphragm has an inner surface which defines a longitudinal lumen within the longitudinal passageway. The longitudinal lumen has a longitudinal axis and the respective expansion chambers and corresponding fluid communication ports are oriented axisymmetrically in respect to the longitudinal axis. In preferred embodiments, the fluid pump is a fluid filled bladder within an innervated skeletal muscle pouch. The skeletal muscle pouch is preferably created surgically from a latissimus dorsi muscle flap which is preferably generated during a prior surgical procedure. The fluid filled bladder communicates with the EAB pump via fluid communication conduits and the fluid communication ports. Contraction of the skeletal muscle pouch is stimulated by an implantable pulse train generator which is synchronized with the beating of the active heart. Methods of assisting an active heart using the disclosed implantable heart assist device are also disclosed.

32 Claims, 3 Drawing Sheets

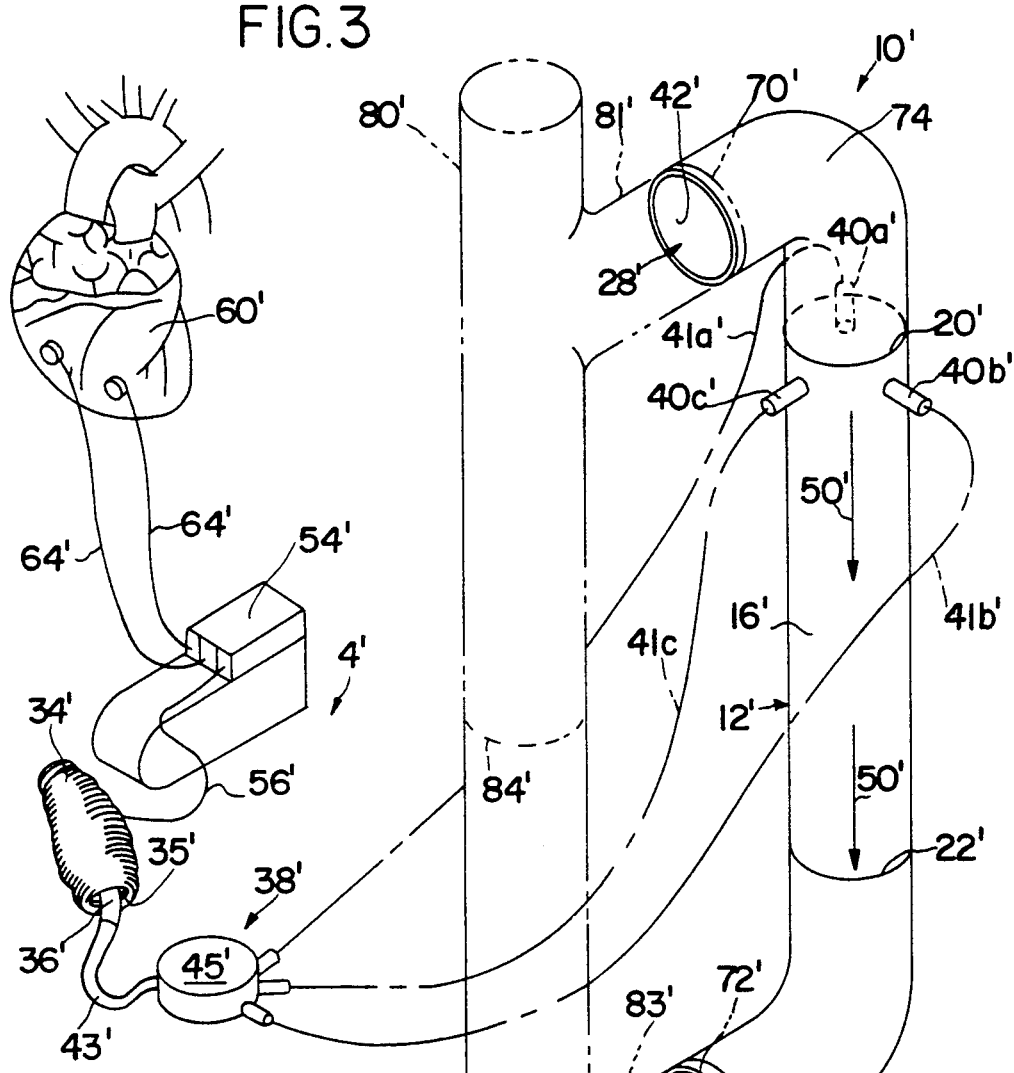
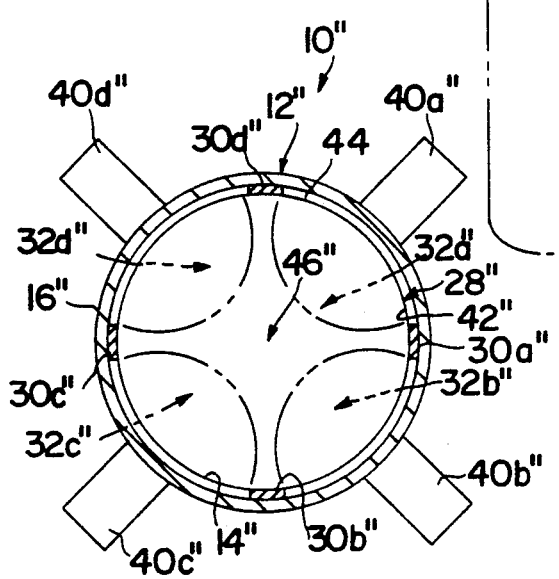

IMPLANTABLE HEART-ASSIST DEVICE

BACKGROUND OF THE INVENTION

The present invention relates to implantable heart-assist devices, specifically heart assist devices including extra-aortic balloon (EAB) pumps for providing assistance to an active heart. The present invention is particularly related to EAB pumps used in conjunction with an internal fluid pump, such as a fluid filled bladder/skeletal muscle pouch type pump such as that disclosed by Stephenson et al. (U.S. Pat. No. 4,979,936), further referenced hereinbelow.

Heart-assist devices are well known in the art. Leachman, Jr. (U.S. Pat. Nos. 3,911,897 and 3,911,898) disclose a heart-assist device including a blood pump which is connected serially between a heart ventricle and the vascular system. During normal operation, the pump is used to maintain a programmed pressure at the ventricle discharge during systolic cardiac pulsation. A pressure transducer detects the pressure at the discharge and controls the pump through a hydraulically powered, closed-loop servomechanism.

Poirier (U.S. Pat. Nos. 4,023,468 and 4,133,616) disclose a blood pump stroke volume limiter for use with a collapsible wall blood pump system. The nomadic pump is adapted primarily as a left ventricle heart-assist device and has a flexible bladder within a rigid housing. A nomadic driver applies rhythmic pulses between the bladder and the housing to repetitively collapse the bladder and establish a pumping action through the bladder, in conjunction with check valves in the inlet and outlet to the bladder. Robinson et al. (U.S. Pat. No. 4,240,409) disclose a circulatory assist device including a valveless pump with a flexible bladder. A pneumatic driver similar to that disclosed by Poirier in U.S. Pat. Nos. 4,023,468 and 4,133,616, and a flexible conduit for conveying blood between the patient and the pump. Preferably, in use, the pump and driver are mounted to the patient's body.

Solonina (U.S. Pat. No. 4,704,120) discloses a one-piece prothesis for biventricular cardiac assistance and reanimation which is preferably implanted in the right hemithorax between the diaphragm and the right lung. The prothesis includes a one-piece shell and two blood circulating deformable-diaphragm pumps actuated by fluid, preferably a compressed gas.

Kolff (U.S. Pat. No. 4,838,889) discloses a ventricle assist device including a housing an atrial chamber, an atrial compliance chamber, a ventricle chamber and a ventricle pumping chamber. A pumping member within the housing separates the ventricle blood chamber from the ventricle pumping chamber and is displaced by a drive fluid to expel blood out of the ventricle blood chamber through an outlet port.

Wampler (U.S. Pat. No. 4,906,229) discloses a high-frequency transvalvular blood pump preferably for temporary cardiac assist which provides suction to decompress the ventricle cavity during both systole and diastole. The intake end of the pump is preferably connected to a cannula which is inserted into the ventricle cavity through the aortic valve. The pump consists of a stiff barrel whose interior volume can be alternately reduced and expanded by a flexible membrane preferably controlled by pneumatic pressure from an extracorporeal location through a percutaneously inserted lumen.

Jarvik (U.S. Pat. No. 4,938,766) disclose a plurality of representative prosthetic arterial compliance chambers (PACCs). In principle, a PACC device is disclosed to be a blood containing chamber that changes in volume as a function of a pressure which is applied. The devices disclosed include, but are not limited to, a generally rigid device such as a cylinder with a spring loaded piston, an elastic device such as a stretchable balloon, or a resilient deformable device such as a flattened tube. Jarvik teaches that the device must be connected to a blood vessel and designed to avoid blood damage and thrombosis.

It will be appreciated that Jarvik's concern about avoiding blood damages and thrombosis are concerns shared by all of those skilled in the art of providing heart-assist devices. It will be further appreciated that this is presently an area of significant experimentation and that damage to the blood and unnatural movement of blood fluids through a heart-assist device may result in thrombosis and other life-threatening events.

Khalafalla (U.S. Pat. No. 4,813,952) discloses a muscle-powered pump to assist an active heart. The device comprises an oblate, spheroidal-shaped pumping chamber surrounded by innervated skeletal muscle tissue and can be coupled to a ventricle and the descending aorta with valves stimulated in synchrony with the natural depolarization of the heart, or inserted into the descending aorta and used as a counterpulsation device. Of the configurations for counterpulsation, one employs an essentially blind-ended pumping chamber which would be likely to present a high risk for causing thrombosis, because blood could be expected to stop flowing momentarily in the dead space at the end of the chamber when the muscle tissue is not contracting. Another utilizes skeletal muscle tissue wrapped directly around the aorta. This would present problems following surgical implementation, because there is very little space on the aorta around which to wrap the skeletal muscle without disrupting the flow of blood to the spinal cord through the numerous vertebral branches of the aorta. If it is necessary to ligate any of the vertebral branches, a significant risk of subsequent paraplegia is created.

Stephenson et al. (U.S. Pat. No. 4,979,936) disclose a heart-assist apparatus including an innervated skeletal muscle pouch which surrounds a collapsible, shape-retaining bladder. The bladder is interconnected to a second bladder enclosed in a sheath around a portion of the descending aorta. The bladders are filled with a fluid such that when the skeletal muscle contracts in response to an electrical stimulation, the fluid is forced from the first bladder to the bladder sheathed with the aorta, expanding that bladder and forcing the aorta to compress. Although quite creative, limited access to the aorta due to the numerous vertebral branches still presents a problem. It will be appreciated, therefore, that there continues to be a need for heart-assist devices which can be employed without creating risks for heart-assist devices which can be employed without creating risks for thrombosis, paraplegia or other potentially debilitating or life threatening conditions.

All of the heart-assist devices disclosed hereinabove are believed to devices for which experimentation is either continuing or under further evaluation. It will be appreciated that the complexities of cardiac implantation, vascular thrombosis and vascular fluid mechanics continue to have uncertainties which require further experimentation and understanding before settled procedures for providing safe and reliable assistance to the active heart will be available to medical practitioners and the public.

In this context, the present invention is directed to an extra-aortic balloon pump which improves upon the teachings of the prior art disclosed above, and addresses further problems associated with heart-assist devices and other related devices and methods, and solves other problems associated therewith.

SUMMARY OF THE INVENTION

The present invention provides an extra-aortic balloon pump for use in cooperation with a separate fluid pump. The extra-aortic balloon (EAB) pump comprises a rigid housing, a flexible, generally cylindrical diaphragm, and means for securing the diaphragm to the rigid housing. The rigid housing includes interior and exterior surfaces, proximal and distal ends, and a longitudinal passageway defined by the interior surface and extending through the rigid housing. The flexible, generally cylindrical diaphragm has inner and outer surfaces and resides generally within the longitudinal passageway, wherein the inner surface defines a longitudinal lumen within the longitudinal passageway and the longitudinal lumen extends through the extra-aortic balloon pump, wherein said securing means secure the diaphragm to the rigid housing so as to create a plurality of separate expansion chambers, wherein each of said plurality of expansion chambers are individually defined by one of a plurality of individual portions of the interior surface in cooperation with one of a plurality of individual segments of the outer surface and said securing means. The flexible, generally cylindrical diaphragm includes a plurality of balloon portions individually enclosing corresponding expansion chambers against the interior surface, wherein said extra-aortic balloon pump further comprises fluid communication means for separately exchanging fluid between each of said plurality of expansion chambers and the fluid pump. The fluid pump is in communication with each of the respective expansion chambers via said fluid communication means, wherein the respective expansion chambers can be expanded when fluid is directed into the respective expansion chambers by the fluid pump. In preferred embodiments, the rigid housing is a straight, generally cylindrical housing, the longitudinal lumen has a longitudinal axis, and/or the respective expansion chambers are generally axisymmetric in respect to the longitudinal axis within a transverse, preferably any transverse, cross-section of the extra-aortic balloon pump. Preferably, said fluid communication means include a plurality of fluid communication ports, wherein each of said plurality of expansion chambers is in fluid communication with the fluid plump via one of said plurality of fluid communication ports.

In further preferred embodiments, each of said plurality of fluid communication ports communicates with one of the plurality of expansion chambers at one of a plurality of positions along the exterior surface of the rigid housing, which are equidistant from each of the respective distal and proximal ends and axisymmetrically oriented about the housing in respect to the longitudinal axis. Preferably, each of the plurality of positions along the exterior surface is closer to one of the respective ends of the housing, wherein the respective expansion chambers expand proximate that end prior to expanding proximate the other end when fluid passes simultaneously into each of the plurality of expansion chambers via the respective fluid communication ports.

The plurality of balloon portions preferably expand simultaneously, first, proximate the end nearest to the plurality of fluid communication ports and, second, proximate the other end so as to create generally axisymmetric peristaltic waves along the inner surface of the flexible diaphragm proximate each respective balloon portion in respect to the longitudinal axis. In use, this end is the proximal end, and the proximal end is grafted into the vascular system more proximate the heart than the distal end so that blood generally flows through the EAB pump from the proximal end to the distal end.

The preferred EAB pump of the present invention is grafted into the descending aorta in parallel therewith. Preferably, curved end extension members are provided to eliminate the risk of any kinking in the conduits extending from the descending aorta to the EAB pump of the present invention. The preferred heart-assist device includes a innervated skeletal muscle pouch which is surgically constructed from a latissimus dorsi muscle flap using surgical procedures which are well-known in the art. The skeletal muscle pouch is electrically stimulated to contract by a pulse train generator which is synchronized with the beating of the active heart. When the muscle pouch contracts, it compresses a fluid-filled, shape-retaining collapsible bladder which communicates with the respective expansion chambers via fluid communication conduit means. In response to the compression of the fluid-filled bladder, the expansion chambers expand, thereby driving blood in preferred EAB pump through the longitudinal lumen in the direction of the distal end where it exits into the downstream vascular system.

The preferred EAB pump of the present invention is designed to generate flow patterns which are believed to be an improvement over the prior art flow patterns which have been shown to be thrombogenic in certain instances. It is believed that the generally straight lumen of the present EAB pump may eliminate some of the flow problems which exist in prior art pumps, and thereby minimize thrombosis problems which have arisen on occasion when using such prior art pumps. The blood flow through the present EAB pump will be essentially laminar, and all of the inner surfaces of the generally cylindrical diaphragm, which define the longitudinal lumen passing through the present pump, will be washed, thereby minimizing or preventing stagnation and potentially thrombogenic conditions within the pump. It is believed that turbulence within the pump will be either minimized or eliminated. Therefore, by maintaining generally laminar flow through the present EAB pump, and minimizing or eliminating turbulence therein, thrombogenic conditions can be minimized or eliminated.

Furthermore, in preferred embodiments, the diaphragm is secured to the rigid housing in a manner which prevents any portion of the inner surface of the diaphragm from coming into contact with another portion thereof when the respective expansion chambers are fully expanded during normal use. In this way, laminar flow will continue through the longitudinal lumen even when the respective expansion chambers are fully expanded. As a result, damage to blood components caused by hemolysis, or other damage from physical impacts upon surfaces within the pump, will be minimized or eliminated. This will further minimize the risk of creating thrombogenic conditions within the pump and the vascular system. Preferably, the pump will provide an assist to the heart, driving blood out of the pump following cardiac systole. This is accomplished by synchronizing the implantable pulse train generator with the electrical impulses of the active heart such that the repetitive contraction of the innervated skeletal muscle pouch is repetitively initiated at or immediately prior to the beginning of cardiac diastole. Because the expansion chambers are oriented axisymmetrically in respect to the longitudinal axis of the longitudinal lumen, it is believed that a laminar flow pattern will be generated within the center of the longitudinal lumen. In the preferred embodiment, having at least three axisymmetric expansion chambers, the laminar blood flow through the longitudinal lumen will prevent stagnation and eliminate the likelihood of thrombosis which has occurred in many of the prior art devices. In preferred embodiments, the heart-assist device of the present invention will provide a repetitive peristaltic counterpulsation device assisting the active heart as needed when employed, but minimizing the risk of thrombosis.

The above-described features and advantages, along with various advantages and features of novelty are pointed out with particularity in the claims of the present application. However, for a better understanding of the invention, its advantages, and objects obtained by its use, reference should be made to the drawings which form a further part of the present application, and to the accompanying descriptive material in which there is illustrated and described preferred embodiments of the present invention.

BRIEF DESCRIPTION OF THE DRAWINGS

In the drawings, in which like and primed reference numerals indicate corresponding parts or elements of preferred embodiments of the present invention throughout the several views;

FIG. 3 is a generally isometric side view of an alternate embodiment of the preferred heart-assist device of the present invention presented in FIG. 1 similar to the view shown in FIG. 1, except that the EAB pump is grafted into the descending aorta in parallel therewith; and FIG. 4 is a generally transverse cross-sectional view of an alternative EAB pump of the present invention similar to the view shown in FIG. 2;

DETAILED DESCRIPTION OF THE PREFERRED EMBODIMENTS

As required, detailed embodiments of the present invention are disclosed herein. However, it is to be understood that the disclosed embodiments are merely exemplary of the present invention, which may be embodied in alternative embodiments that fall within the broad principles of the present invention as set forth in the claims attached hereto. Therefore, specific details disclosed herein are not to be interpreted as limiting, but rather as a basis for the claims and as a representative basis for teaching one of skill in the art to variously practice the present invention.

Figure 1:
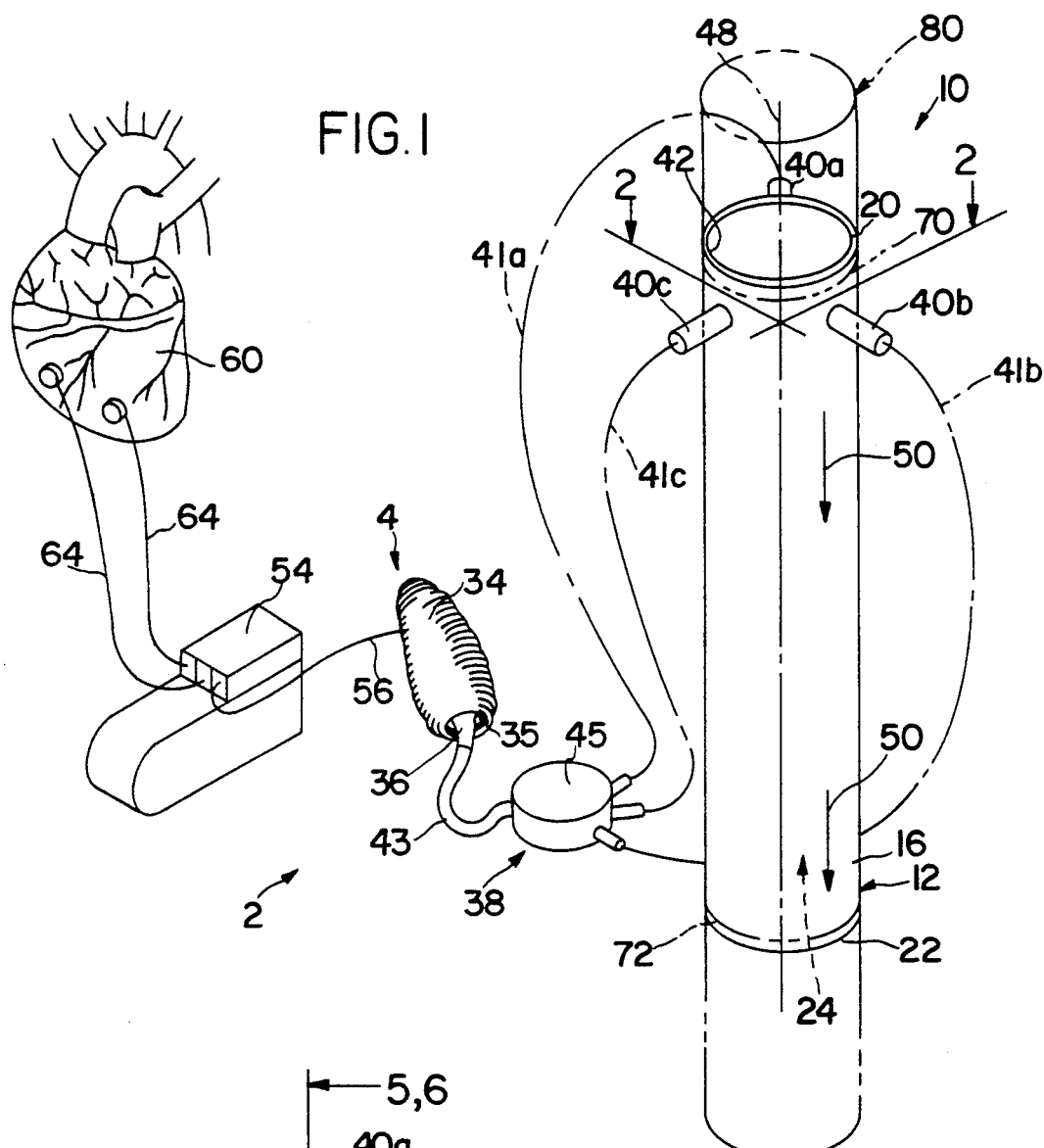
FIG. 1 is a generally schematic isometric view of an implantable heart-assist device including an extra-aortic balloon (EAB) pump driven by a separate pump including a collapsible bladder in an innervated skeletal muscle pouch in accordance with the present invention, wherein the EAB pump is grafted into the descending aorta in series therewith.
Figure 2:
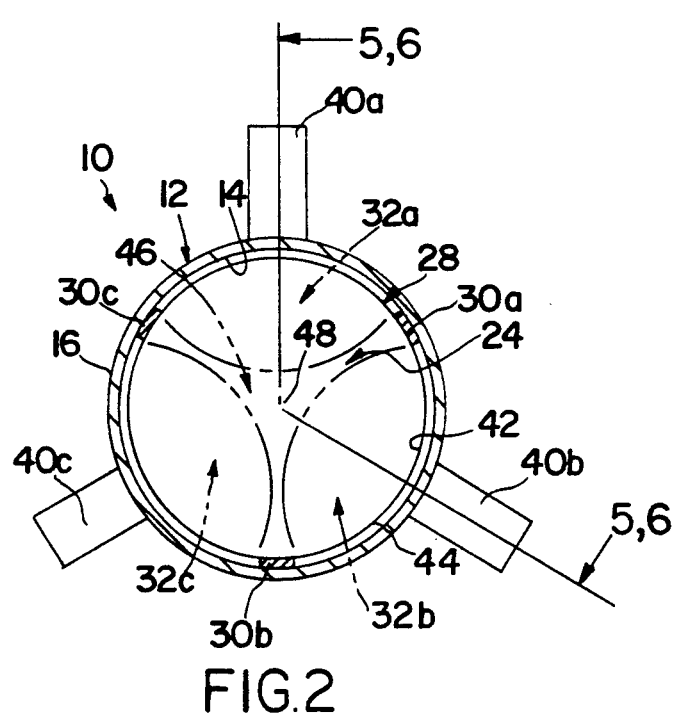
FIG. 2 is a generally schematic transverse cross-sectional view of the EAB pump of FIG. 1 as seen from the line 2—2 of FIG. 1, except that the expansion chambers of the EAB pump are fully expanded as they would be during normal use.

Referring now to the figures, and specifically to FIGS. 1 and 2, FIG. 1 generally presents a schematic representation of a preferred heart-assist device (2) which includes a fluid pump (4) and an extra-aortic balloon (EAB) pump (10) in accordance with the present invention. FIG. 2 presents a schematic representation of a transverse cross-section of the EAB pump (10) shown in FIG. 1. The EAB pump (10) includes a rigid, generally cylindrical housing (12) having interior and exterior surfaces (14 and 16, respectively), proximal and distal ends (20 and 22, respectively), and a longitudinal passageway (24) passing through the center of the cylindrical housing (12). In preferred embodiments, the rigid housing (12) is made of a biocompatible material which is considered to be suitable for being implanted into humans. However, it is not essential for the rigid housing (12) to be cylindrical, as other configurations can be used so long as they are suitable for implanting, for being grafted into an individual's vascular system, for minimizing turbulence and maximizing laminar blood flow through the pump (10), and for providing other essential elements of the EAB pump (10).

The EAB pump (10) further includes a flexible, generally cylindrical diaphragm (28) which resides within the longitudinal passageway (24) and is secured to the rigid housing (12) at the proximal and distal ends (20 and 22, respectively) of the housing (12) and along longitudinal engagement strips (30a, 30b and 30c). In preferred embodiments, the generally cylindrical diaphragm (28) is secured to the rigid, cylindrical housing (12) using an adhesive, preferably a medical grade silicone adhesive, such as Dow-Corning Silicone Medical Adhesive, Dow-Corning Co., or most preferably Raumedic Adhesive, from Rehau Co., West Germany. The preferred flexible diaphragm (28) of the present invention is made of resilient, shape-retaining, biocompatible synthetic material such as polyurethanes, silicone elastomers, fluoroelastomers, polyolefin rubber and the like. Of these materials, polyurethane is the most preferred, preferably Biolon ™ from E. I. Dupont DeNemours and Co., Inc., Waynesboro, Va. Preferably, the inner surface (42) is treated or coated with thromboresistant agents or surface treatments, such as heparin or the like. The generally cylindrical rigid housing (12) is preferably made of a biocompatible synthetic material such as polycarbonate, polysulfone, polyurethane, epoxy, polyethylene, polystyrene, acrylic, polysulfones and polycarbonates are the most preferred, preferably polysulfone, most preferably Udel ™ from Amoco Performance Products, Inc., Ridgefield, Conn.

The longitudinal engagement strips (30a, 30b and 30c) effectively separate three expansion chambers (32a, 32b and 32c). The cylindrical diaphragm (28) has an inner surface (42) and an outer surface (44). The inner surface defines a longitudinal lumen (46) having a longitudinal axis (48). The expansion chambers (32a, 32b and 32c) and the fluid communication ports (40a, 40b and 40c) are oriented axisymmetrically in respect to the longitudinal axis (48). In preferred embodiments, the longitudinal lumen (46) is generally straight and the plurality of expansion chambers (32a, 32b and 32c) are oriented axisymmetrically in respect to the longitudinal axis (48), and preferably has an internal diameter (ID) of about 5–40, preferably about 10–30, more preferably about 20–25 mm in order to generally match the ID of the descending aorta (80) or wherever the pump (10) is to be inserted within the vascular system. The EAB pump (10) is designed to encourage a continuous laminar flow of blood through the lumen (46). The longitudinal engagement strips (30a, 30b and 30c) extend the length of the interior surface (14) of rigid housing (12), and preferably have a width sufficient to minimize or eliminate the likelihood that opposing portions of the inner surface (42) will come into contact with each other during normal use of the EAB pump (10).

The fluid pump (4) includes an innervated skeletal muscle pouch (34) having a partially enclosed center (35) in which a fluid-filled, shape-retaining bladder (36) is inserted. A fluid (not shown) in the bladder (36) communicates with each of the respective expansion chambers (32a, 32b and 32c) of the EAB pump (10) via a fluid communication conduit (38) which is interconnected with a plurality of fluid communication ports (40a, 40b and 40c) on the rigid housing (12). The fluid (not shown) can be any fluid which is suitable for the intended purpose, preferably a liquid, preferably a liquid such as an aqueous saline solution, a silicone oil, a perfluorinated liquid or the like, most preferably an aqueous saline solution. The fluid communication conduit (38) includes a plurality of port conduits (41a, 41b and 41c) joined to a single bladder conduit (43) by a conduit manifold (45), each of which are preferably made of a biocompatible medical grade materials such as silicone rubber, polyethylene, fluorocarbon, polypropylene and the like. The port conduits (41a, 41b and 41c) and the bladder conduit (43) are preferably silicone rubber tubes, most preferably, Medical Grade Silicone Tubing from Baxter Travenol, McGraw Park, Ill. In preferred embodiments, the fluid communication ports (40a, 40b and 40c) have an inside diameter (ID) of about 5–10, preferably about 6–8 mm in order to allow the fluid (not shown) to flow easily between the expansion chambers (32a, 32b and 32c) and the fluid pump (4). These ports (40a, 40b, and 40c) are also located closer to the proximal end (20) of the rigid housing (12) than to the distal end (22), in order that portions of the respective expansion chambers (32a, 32b and 32c) proximate the proximal end (20) will expand in response to a contraction of the muscle pouch (34) before portions of the respective expansion chambers more removed from the proximal end (20) toward the distal end (22). In this way, it is anticipated that a peristaltic fluid pumping action will be provided, with a plurality of peristaltic waves along portions of the inner surface (42) of the diaphragm (28) proximate the respective expansions chambers (32a, 32b and 32c) forcing blood (not shown) in the longitudinal lumen (46) in the direction of the distal end (22). These peristaltic waves will cause the blood to fill the passageway (24) starting with the distal end toward the proximal end in order to decrease the likelihood of drawing blood away from the carotid and coronary arteries.

In another preferred embodiment (not shown) the fluid communication ports (not shown) are located closer to the distal end (not shown). Although further consideration of the location of the respective ports (40) in respect to the respective ends (20 and 22) is ongoing, it is possible that when the ports (40) are oriented axisymmetrically, and located closer to the distal end (22) than the proximal end (20), the assistance provided by the alternate EAB pump (not shown) may provide improved systolic unloading.

The innervated skeletal muscle pouch (34) of the present invention is preferably surgically constructed or created in the patient in which the heart-assist device (2) is to be implanted using surgical methods which are well known in the art. It is preferable to use innervated skeletal muscle to create the muscle pouch (34), however, the muscle pouch need not be innervated. Although the non-innervated muscle pouch may be less desirable and requires a slightly different system for stimulation, such systems, and methods therefor, are well known in the art and may be employed in respect to the present invention. It is noted, however, that the preferred skeletal muscle pouch (34) of the present invention is an innervated skeletal muscle pouch (34) which is surgically created from the patient's latissimus dorsi muscle using procedures that are well known in the art. In this regard, it is noted, that the present invention may include elements of the disclosures presented in U.S. Pat. Nos. 4,813,952 (Khallafala); 4,979,936 (Stephenson et al.); 4,341,221 (Hagfors); and 4,735,205 (Grandjean et al.), each of which is expressly incorporated herein by reference.

The fluid pump (4) further includes an implantable pulse train generator (54) including electrodes, preferably a single bipolar or unipolar electrode (56), interconnected with the muscle pouch (34). In preferred embodiments, the unipolar electrode (56) is attached to the latissimus dorsi nerve (not shown) proximate the point at which the nerve trifurcates. This nerve cuff electrode (56) is used to repetitively, electronically stimulate contraction of the skeletal muscle of the muscle pouch (34).

During operation of the heart-assist device (2) of the present invention when implanted in the individual patient, the implantable pulse train generator (54) is interconnected with the patient's heart (60), preferably, the left ventricle, by monitoring leads (64) so that the contraction of the muscle pouch (34) can by synchronized with the beating of the heart (60). In a preferred embodiment of the present invention, the pulse train generator (54) is a Prometheus ™ Implantable Pulse Generator (IPG) from Medtronic, Inc., Minneapolis, Minn. (product No. 6100). The pulse train generator (54) is preferably synchronized so that the contraction of the muscle pouch (34) begins, either at or immediately prior to, the beginning of cardiac diastole. In this way, the muscle pouch (34) will contract at the beginning of diastole and fluid from the collapsible bladder (36) will pass into the respective expansion chambers (32a, 32b and 32c), via the fluid communication conduit (38) and the fluid communication ports (40a, 40b and 40c), respectively, thereby expanding the expansion chambers (32a, 32b and 32c) and driving blood in the longitudinal lumen (46) in a downstream direction past the distal end (22) of the EAB pump (10), and thereby providing assistance to the active heart (60). The pulse train generator (54) is further synchronized to allow the muscle pouch (34) to relax at the beginning of cardiac systole. When the muscle pouch (34) relaxes, the shape-retaining, collapsible bladder (36) will return to its pre-contraction shape, thereby drawing fluid out of the respective expansion chambers (32a, 32b and 32c) via the fluid communication ports (40a, 40b and 40c, respectively) and the fluid communication conduit (38). The patient's normal blood pressure may provide an additional force assisting the fluid to pass out of the expansion chambers (32a, 32b and 32c) and into the bladder (36) under these conditions. Subsequently, the pulse train generator (54) initiates the repetition of the cycle of events in response to electrical impulses from the heart (60), signaling the respective phases of the cardiac cycle, which is monitored by the pulse train generator (54). It will be appreciated that the fluid communicated between the collapsible bladder (36) the fluid communication conduit (38) and the respective expansion chambers (32a, 32b and 32c) will be a fluid which is suitable for the present task. Although any suitable fluid may be used, a liquid is preferred, preferably as a buffered aqueous solution, such as a saline solution.

In preferred embodiments, the generally cylindrical diaphragm (28) is secured to the respective proximal and distal ends (20 and 22) of the rigid housing (12) by extending the generally cylindrical diaphragm (28) through the longitudinal passageway (24) and over the respective ends (20 and 22) so the ends of the generally cylindrical diaphragm (28) can be folded back over a small portion of the exterior surface (16) of the rigid housing (12) proximate each of the respective ends (20 and 22). The respective ends of the generally cylindrical diaphragm (28) can then be secured to the exterior surface (16) of the rigid housing (12) using an appropriate adhesive, such as the silicone adhesive used to secure the cylindrical diaphragm (28) to the interior surface (14) of the rigid housing (12) in the longitudinal engagement strips (30a, 30b and 30c) described herein above. Alternatively, the diaphragm 28 can be secured either solely to the interior surface (14) proximate the respective ends (20 and 22), or to both the interior and exterior surfaces (14 and 16) proximate the respective ends (20 and 22). Preferably, Silicone Medical Adhesive from Dow-Corning Co., or Raumedic Adhesive, from Rehau Co., West Germany, will be used for both of these purposes. However, it will be appreciated that any suitable, biocompatible, adhesive or bonding material can be used within the scope of the present invention. Furthermore, other methods for securing the generally-cylindrical diaphragm (28) to the rigid housing, in addition to those disclosed herein, may be used without limit in the present invention so long as the EAB pump (10) is considered to be acceptable for the purposes intended.

In preferred embodiments of the present invention, end caps (70 and 72) can be secured to the respective proximal and distal ends (20 and 22) of the rigid housing to further secure the generally cylindrical diaphragm (28) to the rigid housing (12). Although the aorta (80) can be secured to the EAB pump (10) in series as shown in FIG. 1, it is not necessary to provide the end caps (70 and 72). It will be appreciated that the surgical methods used for grafting the EAB pump (10) into the vascular system are well known in the art.

Referring now also to FIG. 3, an alternate embodiment of the preferred heart-assist device (2') is shown. The alternate heart-assist device (2') includes an EAB pump (10') interconnected with a fluid pump (4') in the manner previously disclosed. In the alternate embodiment, however, the EAB pump (10') is grafted into the vascular system in parallel with the descending aorta (80'). Although it is not necessary, the aorta (80') can be ligated at an intermediate position (84') shown by the dashed line (84') between the side exiting and entering vascular grafts (81' and 83', respectively) which are anastomosed to the aorta to interconnect the EAB pump (10') therewith. In order to minimize the risk of kinking in the vascular grafts (81' and 84'), the EAB pump (10') is provided with curved extension members (74' and 76') which are interconnected directly to the rigid, generally cylindrical housing (12') of the EAB pump (10'). The curved extension members (74' and 76') have generally the same inside diameter as the rigid housing (12'). The generally cylindrical diaphragm (28') is extended through each of the curved extension members (74' and 76') so that the longitudinal lumen (46') of the EAB pump (10') is effectively extended into an adjacent curved lumen (78') at each of the respective ends (20' and 22') of the EAB pump (10') in order to provide a consistent blood lining interface. In this embodiment, the end caps (70' and 72'), although, as before, not required, may be provided at the ends of the respective curved end extension members (74' and 76') most removed from the EAB pump (10') It will be appreciated that the expansion chambers (32a', 32b' and 32c') are confined within the length of the rigid housing (12') and do not extend into either of the curved end extension members (74' and 76'). Alternatively, the generally cylindrical diaphragm (28'), after being secured to the rigid housing (12') proximate the respective ends (20' and 22') to form the respective expansion chambers (not shown) which correspond to the expansion chambers 32a, 32b and 32c in FIG. 2 will extend into the curved end extension members (74 and 76) to provide improved hemodynamics. It will be appreciated that the technology used to join the respective elements described immediately herein above is known in the art, and that it is essential only that these elements joined in a manner are effective to permit the satisfactory and efficacious use of the preferred heart-assist devices (2 and 2') of the present invention.

The EAB pump (10) of the present invention can be inserted into a patient's vascular system in a number of locations. Preferably, however, the EAB pump (10) will be grafted into the vascular system proximate the descending aorta (80). The preferred EAB pumps (10 and 10') can be grafted into the vascular system proximate the aorta (80 and 80') either in series, as shown in FIG. 1, or in parallel, as shown in FIG. 3, using standard surgical procedures which are well-known in the art.

Although the preferred embodiment of the present EAB pump (10) provides three axisymmetric expansion chambers (32a, 32b and 32c) and three corresponding fluid communication ports (40a, 40b and 40c, respectively), it will be appreciated that any practical number of axisymmetric expansion chambers and corresponding fluid communication ports may be provided so long as the resulting EAB pump is effective for its intended purpose. In this regard, it is noted that an EAB pump (not shown) having only two corresponding expansion chambers (not shown) and fluid communication ports (not shown) can be in a heart-assist device of the present invention Similarly such a device (not shown) having four, five, six or more corresponding axisymmetric expansion chambers and fluid communication ports may also be used.

Referring now also to FIG. 4, a transverse cross-section of one such EAB pump (10') is shown wherein four corresponding axisymmetric expansion chambers (32a", 32b", 32c" and 32d") and fluid communication ports (40a", 40b", 40c", and 40d") are provided. Referring now specifically to FIGS. 2 and 4, in each of the preferred embodiments of the present EAB pump (10 and 10"), it is essential that the inner surface (42 and 42") of the generally cylindrical diaphragm (28 and 28") not come into contact with itself when the respective expansion chambers (32a, 32b and 32c; and 32a", 32b", 32c" and 32d") are fully expanded. In this way, care is taken to avoid damage to various components to the blood passing through the longitudinal lumen (46 and 46") of the preferred EAB pumps (10 and 10"). This is believed to be important in order to avoid creating thrombogenic conditions which may result in serious risks for the implant patient. It is also believed that it is important, as much as possible, to provide enough space between respective portions of the inner surface (42 and 42") so that blood may flow against every portion of the inner surface (42 and 42") at all times, whether when the respective expansion chambers are fully expanded or fully contracted. It will be appreciated that if components of the blood in the longitudinal lumen (46 and 46') are damaged as a result of a force being applied to the blood component against a surface, or if some other means of damaging the blood component results in the inhibition of the normal passage of the blood, and/or blood components, it is believed that thrombosis may be more likely to occur. Therefore, it is believed to be desirable to limit the risk of such an event by providing ample separation between adjacent portions of the inner surface (42 and 42") of the cylindrical diaphragm (28 and 28") when the respective expansion chambers are fully expanded during normal use.

Figure 6:
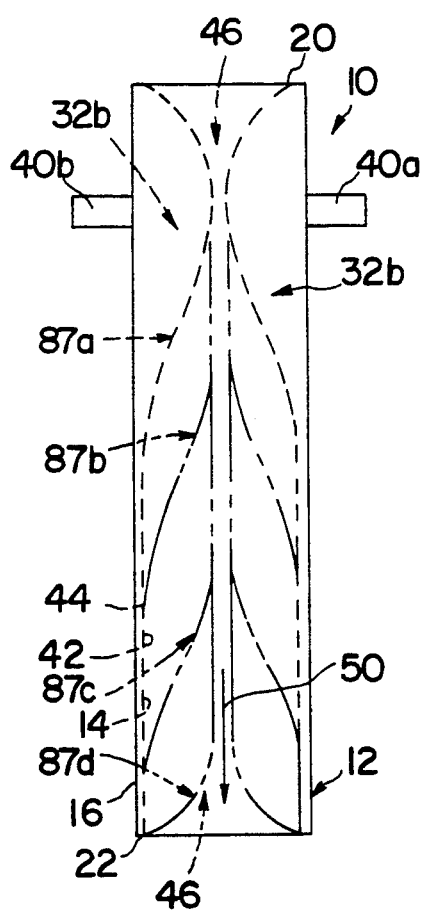
FIG. 6 is a generally schematic side view of the preferred EAB pump of FIG. 2 as seen generally from the line 6—6, except that the diaphragm, shown in the phantom is shown in separate stages of expansion.
Figure 5:
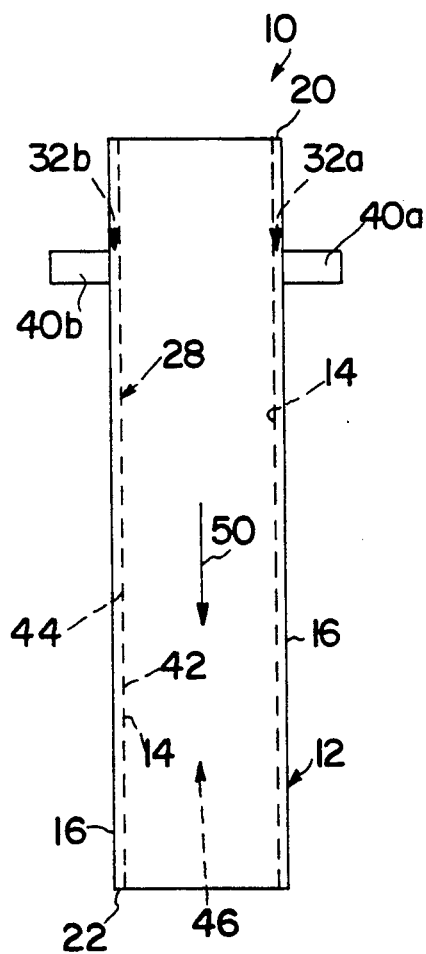
FIG. 5 is a generally schematic side view of the preferred EAB pump of FIG. 2 as seen generally from the line 5—5, except that the diaphragm, shown in the phantom, is in a contracted state.

Referring now also to FIGS. 5 and 6, the EAB pump (10) is designed to provide assistance to the active heart (60) by providing peristaltic pumping action downstream from the heart. The peristaltic pumping action is provided when the axisymmetric expansion chambers (32a, 32b and 32c) expand axisymmetrically in respect to the longitudinal axis (48) starting at a location proximate the fluid communication ports (40a, 40b and 40c), and then downstream toward the distal end as shown specifically by the successive phantom lines (87a, 87b, 87c and 87d) in FIG. 6, which schematically illustrate the sequential, simultaneous, axisymmetric expansion of the respective expansion chambers (32a, 32b and 32c) two of which (32a and 32b) are shown. In FIG. 5, the expansion chambers (32a and 32b) are in a contracted state. During use of the EAB pump (10), however, the expansion chambers (32a, 32b and 32c) are repetitively expanded and contracted in response to the contraction and relaxation of the muscle pouch (34). When the muscle pouch (34) contracts in response to an electrical pulse from the pulse train generator (54), the collapsible bladder (36) is compressed such that it drives fluid (not shown) into the respective expansion chambers (32a, 32b and 32c) at an equal rate under an equal fluid pressure. The respective expansion chambers will expand first proximate the respective fluid communication ports (40a, 40b and 40c). As shown schematically in FIG. 6, the diaphragm (28) will initially take the general cross-sectional shape of dashed line (87a), and subsequently As the expansion of the expansion chambers continues to proceed the diaphragm will expand further as represented by dashed line (87c) and will eventually will be fully expanded to take the cross-sectional general shape of dashed line (87d). In this way, the EAB pump (10) can provide a peristaltic pumping action to assist blood fluid (not shown) through the lumen (46) in the direction of the distal end (22).

It will be understood, however, that even though these numerous characteristics and advantages of the invention have been set forth in the foregoing description, together with details of the structure and function of the present invention, the disclosure is illustrative only, and changes may be made in detail, especially in matters of shape, size, and arrangement of the parts within the broad principles of the present invention to the full extent indicated by the broad general meaning of the terms in which the appended claims are expressed.

What is claimed is:

1. An extra-aortic balloon pump for use in cooperation with separate fluid pump means, said extra-aortic balloon pump comprising:
   (a) a rigid housing including interior and exterior surfaces, proximal and distal ends, and a longitudinal passageway defined by the interior surface and extending through the rigid housing;
   (b) a flexible, generally cylindrical diaphragm having inner and outer surfaces and residing generally within the longitudinal passageway, wherein the inner surface defines a longitudinal lumen within the longitudinal passageway, the lumen extending through said extra-aortic balloon pump; and
   (c) means for securing the diaphragm to the rigid housing, wherein said securing means secure the diaphragm to the rigid housing so as to create a plurality of separate (comma) substantially parallel expansion chambers, wherein each of said plurality of expansion chambers are individually defined by one of a plurality of individual portions of the interior surface of the rigid housing in cooperation with one of a plurality of individual segments of the outer surface of the diaphragm and said securing means, wherein the diaphragm includes a plurality of balloon portions individually enclosing corresponding expansion chambers against the interior surface, wherein said extra-aortic balloon pump further comprises fluid communication means for separately exchanging fluids between each of the plurality of expansion chambers and said fluid pump means, wherein said fluid pump means are in communication with each of the respective expansion chambers via said fluid communication means, and wherein the respective expansion chambers can be expanded when fluid is directed into the respective expansion chambers.

2. The extra-aortic balloon pump of claim 1, wherein the lumen has a longitudinal axis and the respective plurality of expansion chambers are generally axisymmetric in respect to the longitudinal axis within a transverse cross-section of said extra-aortic balloon pump.

3. The extra-aortic balloon pump of claim 2, wherein the respective plurality of expansion chambers are generally axisymmetric in respect to the longitudinal axis within any transverse cross-section of said extra-aortic balloon pump.

4. The extra-aortic balloon pump of claim 3, wherein said fluid communication means include a plurality of fluid communication ports, wherein each of said plurality of expansion chambers is in fluid communication with one of said plurality of fluid ports.

5. The extra-aortic balloon pump of claim 4, wherein each of said plurality of fluid ports communicate with one of said plurality of expansion chambers through said rigid housing.

6. The extra-aortic balloon pump of claim 5, wherein each of said plurality of fluid ports communicates with one of said plurality of expansion chambers at one of a plurality of positions along the exterior surface of the rigid housing, which are equidistant from each of the respective proximal and distal ends of the rigid housing and axisymmetrically oriented about the housing in respect to the longitudinal axis of the longitudinal lumen.

7. The extra-aortic balloon pump of claim 6, wherein each of said plurality of positions along the exterior surface of the rigid housing is closer to one of said respective proximal and distal ends of said rigid housing, wherein the respective expansion chambers expand proximate said one of said respective proximal and distal ends prior to expanding proximate the other of said respective proximal and distal ends when fluid passes simultaneously into each of said plurality of expansions chambers via the respective fluid ports, and wherein said plurality of balloon portions expand simultaneously, first, proximate said one of said respective proximal and distal ends, and, second, proximate the other of said respective proximal and distal ends so as to create generally axisymmetric peristaltic waves along the inner surface of the flexible diaphragm proximate each respective balloon portion in respect to the longitudinal axis.

8. The extra-aortic balloon pump of claim 7, wherein each of the respective plurality of balloon portions have a first, generally contracted position and a second, generally expanded position, wherein the inner surface of the flexible diaphragm proximate each respective balloon portion is sufficiently removed from the inner surface proximate each other respective balloon portion so that fluid can pass against the entire inner surface of the flexible diaphragm when passing through the longitudinal lumen when the respective plurality of balloon portions are in the second, generally expanded position.

9. The extra-aortic balloon pump of claim 8, wherein each of said plurality of expansion chambers theoretically have an infinite number of intermediate positions between said first, generally contracted position and said second, generally expanded position, and wherein the respective expansion chambers are generally axisymmetric in respect to the longitudinal axis within any transverse cross-section of said extra-aortic balloon pump when in any of said first or second positions or any of said theoretically infinite number of intermediate positions.

10. The extra-aortic balloon pump of claim 9, wherein the plurality of expansions chambers are three in number, and the plurality of fluid ports are three in number, each of which is axisymmetrically oriented in respect to the longitudinal axis.

11. The extra-aortic balloon pump of claim 10, wherein the flexible, generally cylindrical diaphragm is made of a resilient, biocompatible synthetic material which can expand and contract.

12. The extra-aortic balloon pump of claim 11, wherein the biocompatible synthetic material is polyurethane.

13. The extra-aortic balloon pump of claim 11, wherein the rigid housing and the longitudinal lumen are generally straight.

14. The extra-aortic balloon pump of claim 13, further including a plurality of curved end extension members, the curved end extension members including a first end extension member interconnected with the proximal end of the rigid housing, and a second end extension member interconnected with the distal end of the rigid housing, wherein the respective curved end extension members each define a curved lumen in communication with the longitudinal lumen, wherein the longitudinal lumen is generally straight and the respective curved end lumens are curved.

15. The extra-aortic balloon pump of claim 11, wherein said securing means include a bonding agent capable of securing portions of the outer surface of the flexible diaphragm to portions of the interior surface of the rigid housing.

16. The extra-aortic balloon pump of claim 15, wherein said bonding agent is a silicone adhesive.

17. An extra-aortic balloon pump, comprising:
(a) a rigid housing having interior and exterior surfaces, proximal and distal ends, and a longitudinal passageway extending therebetween; and
(b) a generally cylindrical, flexible diaphragm, wherein the generally cylindrical diaphragm is secured to said rigid housing so as to provide an inner lining for said longitudinal passageway, said inner lining defining a longitudinal lumen passing through the rigid housing within the longitudinal passageway, wherein the generally cylindrical diaphragm is secured to the interior surface of the rigid housing so as to separate a plurality of expansion chambers defined by separate portions of the generally cylindrical diaphragm in cooperation with separate segments of the interior surface of the rigid housing, the rigid housing including a plurality of fluid communication ports, wherein said plurality of fluid communication ports and said plurality of expansions chambers are equal in number and wherein each of said plurality of fluid communication ports is in fluid communication with one of said plurality of expansion chambers such that fluid can pass into and out of each of the respective expansion chambers via a corresponding compression port, wherein the longitudinal lumen is generally straight and has a longitudinal axis, wherein said plurality of fluid communication ports and said plurality of expansion chambers are separately axisymmetric in respect to the longitudinal axis.

18. The extra-aortic balloon pump of claim 17, wherein the fluid communication ports are each an equal distance from each of the respective proximal and distal ends and displaced closer to one of said respective ends than the other, wherein the respective expansion chambers expand proximate the end of the rigid housing closest to the plurality of fluid communication ports when the expansion chambers expand in response to the passage of an expansion fluid into the respective expansion chambers via the respective fluid communication ports.

19. The extra-aortic balloon pump of claim 18, wherein the inner lining of the longitudinal passageway proximate each respective expansion chamber can move generally inwardly toward the longitudinal axis of the longitudinal lumen in response to the passage of the expansion fluid into the respective expansion chambers via the respective fluid communication ports, and wherein segments of the inner lining proximate each respective expansion chamber and more proximate the corresponding fluid communication port can move inwardly toward the longitudinal axis prior to other segments of the inner lining more removed from the corresponding fluid communication ports such that the respective segments of the inner lining will move toward the longitudinal axis in a manner which creates a peristaltic wave which extends longitudinally along the inner lining in a direction away from the segment of the inner lining most proximate the respective fluid communication port toward other segments thereof further removed therefrom.

20. An extra-aortic balloon pump, comprising:
(a) a rigid housing having interior and exterior surfaces, proximal and distal ends, and a longitudinal passageway defined by the interior surface and extending longitudinally through the rigid housing; and
(b) flexible fluid separation means interconnected with said rigid housing, said flexible fluid separation means including an inner surface which defines a longitudinal lumen passing through the longitudinal passageway and having a longitudinal axis, wherein said flexible fluid separation means cooperates with the rigid housing to define a plurality of expansion chambers separated from the longitudinal lumen by said flexible fluid separation means, said rigid housing further including a fluid communication port communicating with each of said plurality of expansion chambers, wherein fluid can pass into or out of each of said plurality of expansion chambers via the respective corresponding fluid communication ports to expand or contract the respective expansion chamber and thereby respectively decrease or increase a fluid volume of the longitudinal lumen, wherein the plurality of expansion chambers and the plurality of corresponding fluid communication ports are oriented axisymmetrically in respect to the longitudinal axis.

21. The extra-aortic balloon pump of claim 20, wherein said flexible fluid separation means includes an expandable diaphragm, and wherein the expandable diaphragm expands in response to an expansion of any of said expansion chambers.

22. The extra-aortic balloon pump of claim 21, further comprising fluid delivery means for delivering and removing an expansion fluid to each of the respective expansion chambers via the corresponding fluid communication ports, wherein each of said plurality of expansion chambers have an expandable chamber volume, wherein the expansion or contraction of the respective expansion chamber can be coordinated so that the chamber volume of each respective expansion chamber can be expanded or contracted simultaneously with the expansion or contraction of the respective remaining expansion chambers.

23. The extra-aortic balloon pump of claim 22, wherein the transverse cross-sections of the plurality of expansion chambers are axisymmetric in respect to the longitudinal axis when fully expanded in normal use.

24. The extra-aortic balloon pump of claim 23, wherein each of the plurality of fluid communication ports are located an equal distance from each of the respective ends of the rigid housing, wherein each of the plurality of fluid communication ports are closer to one of the respective ends, and wherein the respective fluid communication ports are axisymmetrically oriented in respect to the longitudinal axis.

25. An extra-aortic balloon pump for use in cooperation with separate fluid pump means, said extra-aortic balloon pump comprising:
(a) a rigid housing including interior and exterior surfaces, proximal and distal ends, and a longitudinal passageway defined by the interior surface and extending through the rigid housing;
(b) a flexible, generally cylindrical diaphragm having inner and outer surfaces and residing generally within the longitudinal passageway, wherein the inner surface defines a longitudinal lumen within the longitudinal passageway, the lumen extending through said extra-aortic balloon pump; and
(c) means for securing the diaphragm to the rigid housing, wherein said securing means secure the diaphragm to the rigid housing so as to create a plurality of separate expansion chambers, wherein each of said plurality of expansion chambers are individually defined by one of a plurality of individual portions of the interior surface of the rigid housing in cooperation with one of a plurality of individual segments of the outer surface of the diaphragm and said securing means; wherein the diaphragm includes a plurality of balloon portions individually enclosing corresponding expansion chambers against the interior surface; wherein said extra-aortic balloon pump further comprises fluid communication means for separately exchanging fluids between each of the plurality of expansion chambers and said fluid pump means; wherein said fluid pump means are in communication with each of the respective expansion chambers via said fluid communication means, and wherein the respective expansion chambers can be expanded simultaneously when fluid is simultaneously directed into the respective expansion chambers; wherein the lumen has a longitudinal axis and the respective plurality of expansion chambers are generally axisymmetric in respect to the longitudinal axis within any transverse cross-section of said extra-aortic balloon pump; wherein said fluid communication means include a plurality of fluid communication ports; wherein each of said plurality of expansion chambers is in fluid communication with one of said plurality of fluid ports; wherein each of said plurality of fluid ports communicate with one of said plurality of expansion chambers through said rigid housing; wherein each of said plurality of fluid ports communicates with one of said plurality of expansion chambers at one of a plurality of positions along the exterior surface of the rigid housing, which are equidistant from each of the respective proximal and distal ends of the rigid housing and axisymmetrically oriented about the housing in respect to the longitudinal axis of the longitudinal lumen; wherein each of said plurality of positions along the exterior surface of the rigid housing is closer to one of said respective proximal and distal ends of said rigid housing, wherein the respective expansion chambers expand proximate said one of said respective proximal and distal ends prior to expanding proximate the other of said respective proximal and distal ends when fluid passes simultaneously into each of said plurality of expansions chambers via the respective fluid ports, and wherein said plurality of balloon portions expand simultaneously, first, proximate said one of said respective proximal and distal ends, and, second, proximate the other of said respective proximal and distal ends so as to create generally axisymmetric peristaltic waves along the inner surface of the flexible diaphragm proximate each respective balloon portion in respect to the longitudinal axis; wherein each of the respective plurality of balloon portions have a first, generally contracted position and a second, generally expanded position, wherein the inner surface of the flexible diaphragm proximate each respective balloon portion is sufficiently removed from the inner surface proximate each other respective balloon portion so that fluid can pass against the entire inner surface of the flexible diaphragm when passing through the longitudinal lumen when the respective plurality of balloon portions are in the second, generally expanded position.

26. The extra-aortic balloon pump of claim 25, wherein each of said plurality of expansion chambers theoretically have an infinite number of intermediate positions between said first, generally contracted position and said second, generally expanded position, and wherein the respective expansion chambers are generally axisymmetric in respect to the longitudinal axis within any transverse cross-section of said extra-aortic balloon pump when in any of said first or second positions or any of said theoretically infinite number of intermediate positions.

27. The extra-aortic balloon pump of claim 26, wherein the plurality of expansions chambers are three in number, and the plurality of fluid ports are three in number, each of which is axisymmetrically oriented in respect to the longitudinal axis.

28. An implantable heart-assist device, comprising:
   (a) an extra-aortic balloon pump, including:
      (i) a rigid housing having interior and exterior surfaces, proximal and distal ends, and a longitudinal passageway defined by the interior surface and extending longitudinally through the rigid housing; and
      (ii) flexible fluid separation means interconnected with said rigid housing, said flexible fluid separation means including an inner surface which defines a longitudinal lumen passing through the longitudinal passageway and having a longitudinal axis, wherein said flexible fluid separation means cooperates with the rigid housing to define a plurality of expansion chambers separated from the longitudinal lumen by said flexible fluid separation means, said rigid housing further including a fluid communication port communicating with each of said plurality of expansion chambers, wherein fluid can pass into or out of each of said plurality of expansion chambers via the respective corresponding fluid communication ports to expand or contract the respective expansion chamber and thereby respectively decrease or increase a fluid volume of the longitudinal lumen, wherein the plurality of expansion chambers and the plurality of corresponding fluid communication ports are oriented axisymmetrically in respect to the longitudinal axis; and
   (b) a fluid pump, including:
      (i) a collapsible, fluid-filled, shape-retaining bladder;
      (ii) innervated skeletal muscle pouch, the innervated skeletal muscle pouch having a central, partially enclosed region in which the fluid-filled, collapsible bladder is inserted;
      (iii) fluid conduit communication means for interconnecting the collapsible, fluid-filled bladder with the fluid communication ports of the rigid housing, wherein fluid from the collapsible bladder can communicate with each of the plurality of expansion chambers of the extra-aortic balloon pump via said fluid conduit communication means; and
      (iv) an implantable pulse train generator including a nerve cuff electrode, wherein the nerve cuff electrode is attached to the innervated skeletal muscle pouch such that an electrical pulse train can be transmitted to the innervated skeletal muscle pouch to stimulate repetitive contractions of the innervated skeletal muscle pulse which in turn cause a repetitive compression of the fluid-filled, shape-retaining, collapsible bladder so as to cause a repetitive expansion of each of the plurality of expansion chambers in the extra-aortic balloon pump in response to the repetitive contraction of the innervated skeletal muscle pulse.

29. A method of providing counter pulsation heart assistance to an individual, the individual having an active heart, a vascular system interconnected with the heart including a descending aorta which receives blood from the heart, and a latissimus dorsi muscle, said method comprising the steps of:
   (1) providing an implantable heart-assist device including:
      (a) an extra-aortic balloon pump, including:
         (i) a rigid housing having interior and exterior surfaces, proximal and distal ends, and a longitudinal passageway defined by the interior surface and extending longitudinally through the rigid housing; and
         (ii) flexible fluid separation means interconnected with said rigid housing, said flexible fluid separation means including an inner surface which defines a longitudinal lumen passing through the longitudinal passageway and having a longitudinal axis, wherein said flexible fluid separation means cooperates with the rigid housing to define a plurality of expansion chambers separated from the longitudinal lumen by said flexible fluid separation means, said rigid housing further including a fluid communication port communicating with each of said plurality of expansion chambers, wherein fluid can pass into or out of each of said plurality of expansion chambers via the respective corresponding fluid communication ports to expand or contract the respective expansion chamber and thereby respectively decrease or increase a fluid volume of the longitudinal lumen, wherein the plurality of expansion chambers and the plurality of corresponding fluid communication ports are oriented axisymmetrically in respect to the longitudinal axis; and
      (b) a fluid pump, including:
         (i) a collapsible, fluid-filled, shape-retaining bladder;
         (ii) a skeletal muscle pouch, the skeletal muscle pouch having a central, partially enclosed region in which the fluid-filled, collapsible bladder is inserted;

(iii) fluid conduit communication means for interconnecting the collapsible, fluid-filled bladder with the fluid communication ports of the rigid housing, wherein fluid from the collapsible bladder can communicate with each of the plurality of expansion chambers of the extra-aortic balloon pump via said fluid conduit communication means;

(iv) an implantable pulse train generator including an electrode and heart synchronization means for electrically interconnecting the implantable pulse train generator with the active heart and for synchronizing a repetitive generation of electrical pulses to stimulate the contraction of the muscle pouch with repetitive electrical impulses from the heart, wherein the electrode can be attached to the skeletal muscle pouch such that an electrical pulse train can be transmitted to the skeletal muscle pouch to stimulate repetitive contractions of the innervated skeletal muscle pulse which in turn cause a repetitive compression of the fluid-filled, shape-retaining, collapsible bladder so as to cause a repetitive expansion of each of the plurality of expansion chambers in the extra-aortic balloon pump in response to the repetitive contraction of the skeletal muscle pulse, wherein the step of providing a heart-assist device includes surgically creating the skeletal muscle pulse a surgical procedure using the individuals latissimus dorsi muscle to create a muscle flap which is subsequently joined together to form the skeletal muscle pouch within the individual; and (2) surgically implanting the heart-assist device in the individual, wherein the implantable pulse train generator is interconnected to receive and be synchronized with electrical impulses of the individual's active heart and the electrode is interconnected with the skeletal muscle pouch, wherein the step of implanting includes grafting the extra-aortic balloon pump into the vascular system proximate the descending aorta.

30. The method of claim 29 wherein the step of implanting the heart-assist device includes synchronizing the implantable pulse train generator with the electrical impulses of the active heart such that the repetitive contraction of the innervated skeletal muscle pouch is repetitively initiated at or immediately prior to the beginning of cardiac diastole.

31. A method of implanting a heart-assist device of claim 29 wherein the step of implanting the heart-assist device includes the extra-aorta balloon pump being grafted into the vascular system in series with the descending aorta.

32. A method of implanting a heart-assist device of claim 29 wherein the step of implanting the heart-assist devices includes the extra-aorta balloon pump being grafted into the vascular system in parallel with the descending aorta.

* * * * *

UNITED STATES PATENT AND TRADEMARK OFFICE
CERTIFICATE OF CORRECTION

PATENT NO. : 5,222,980
DATED : June 29, 1993
INVENTOR(S) : Kendra K. Gealow

It is certified that error appears in the above-indentified patent and that said Letters Patent is hereby corrected as shown below:

Col. 3, line 53, "plump" should be --pump--.

Col. 6, line 61 --fluorocarbons, nylon and the like. Of these materials,-- should be inserted after "acrylic".

Col. 11, line 64 --expand to the cross-sectional shape of dashed line (87b).-- should be inserted after "quently".

Col. 12, line 32 (claim 1) "(comma)" should be deleted and --,-- should be inserted.

Signed and Sealed this

First Day of November, 1994

Attest:

BRUCE LEHMAN

Attesting Officer        Commissioner of Patents and Trademarks